(12) United States Patent
Fischer et al.

(10) Patent No.: US 6,433,229 B1
(45) Date of Patent: Aug. 13, 2002

(54) METHOD OF PRODUCING CYCLIC, α, β-UNSATURATED KETONES

(75) Inventors: Rolf Fischer, Heidelberg; Rolf Pinkos, Bad Dürkheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/914,796

(22) PCT Filed: Feb. 28, 2000

(86) PCT No.: PCT/EP00/01640

§ 371 (c)(1), (2), (4) Date: Sep. 5, 2001

(87) PCT Pub. No.: WO00/55108

PCT Pub. Date: Sep. 21, 2000

(30) Foreign Application Priority Data

Mar. 12, 1999 (DE) .......................................... 199 11 169

(51) Int. Cl.$^7$ ............................................... C07C 45/00
(52) U.S. Cl. ........................ 568/343; 568/347; 568/350; 568/392; 568/344; 568/389
(58) Field of Search ................................. 568/343, 347, 568/350, 392, 344, 389

(56) References Cited

U.S. PATENT DOCUMENTS 3,364,264 A    1/1968  Hardman 3,476,808 A  * 11/1969  Etherington, Jr. et al.

* cited by examiner

*Primary Examiner*—Sreeni Padmanabhan
*Assistant Examiner*—Sikarl A. Witherspoon
(74) *Attorney, Agent, or Firm*—Keil & Weinkauf

(57) ABSTRACT

Preparation of cyclic, α,β-unsaturated ketones of formula II by dehydrogenation of cyclic ketones which conform to formula I

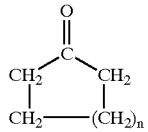
(I)

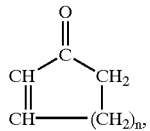

(II)

in which n denotes an integer from 1 to 10, and which may be substituted, at elevated temperature in the presence of catalysts in the vapor phase, wherein the reaction is carried out in the absence of oxygen or in the presence of less than 0.5 mol of oxygen per mol of compound I at temperatures ranging from 250° to 600° C. and using catalysts having a surface area (BET) of more than 0.5 m$^2$/g.

8 Claims, No Drawings

METHOD OF PRODUCING CYCLIC, α, β-UNSATURATED KETONES

This application is a 371 of PCT/EP00/01640, filed Feb. 28, 2000published Sep. 21, 2000.

The present invention relates to a process for the preparation of cyclic, a,p-unsaturated ketones by dehydrogenation of cyclic ketones at elevated temperature in the absence of oxygen or in the presence of less than 0.5 mol of oxygen per mol of starting ketone in the presence of catalysts having a surface area (BET) of at least 0.5 m²/g.

The preparation of cyclic α,β-unsaturated ketones from the corresponding saturated ketones in the vapor phase is described eg for cyclopentenone by F. Delles, J. Am. Chem. Soc. 91, 27 (1969) by uncatalyzed vapor-phase pyrolysis at from 532° to 581° C. in vacuo. However, the cyclopenenone yield and selectivities that can be obtained are very low, since degradation reactions predominate.

U.S. Pat. No. 3,364,264 further describes the conversion of ketones to enones in the vapor phase over oxidation catalysts in the presence of at least one mol of oxygen per mol of ketone. The examples do not reveal what yields or selectivities are achieved, as there are no statements on the overall conversion or by-products. Apart from the actual yields which may be achieved, this process suffers from the basic drawback that when it is dimensioned for large-scale operation special safety measures are necessary, since metering of the large amounts of oxygen is carried out near to or within the explosive limits.

It is thus an object of the present invention to provide a process by means of which cyclic α,β-unsaturated ketones can be continuously synthesized in an industrially simple manner in the vapor phase in high yields without any risk of uncontrolled decomposition.

This object is achieved in the present invention by a process for the preparation, in particular the continuous preparation, of cyclic, α,62 -unsaturated ketones of formula II by dehydrogenation of cyclic ketones which conform to formula I

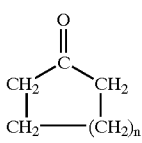
(I)

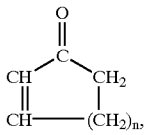
(II)

in which n denotes an integer from 1 to 10, and which may be substituted, at elevated temperature in the presence of catalysts in the vapor phase, where the reaction is carried out in the absence of oxygen or in the presence of less than 0.5 mol of oxygen per mol of compound I at temperatures ranging from 250° to 600° C. and using catalysts having a surface area (BET) of more than 0.5 m²/g.

The cyclic enones and ketones of formulas II and I respectively can carry substituents on the cyclic carbon atoms if desired. Such substituents are eg alkyl or aryl radicals. Preferred starting ketones are cyclohexanone and, in particular, cyclopentanone.

The reaction is preferably carried out in the absence of oxygen, but the reaction may, if desired, be carried out in the presence of specific amounts of oxygen, eg up to 0.2 mol of oxygen per mol of ketone.

The reaction temperatures used in the process of the invention are generally between 2500 and 600° C. and preferably range from 300° to 575° C. and particularly from 350° to 550° C. The reaction pressure is generally between 0.1 and 10 bar and preferably ranges from 0.5 to 6 bar and more preferably from 0.9 to 3 bar.

The conversion of the cyclic ketones can be carried out with or without a carrier gas. If a carrier gas is used, inert gases such as methane, nitrogen and argon are suitable.

If oxygen is to be metered in, this is effected either by metering in air or mixtures of air with inert gas or metering in pure oxygen or mixtures of oxygen with inert gases. During this operation the molar ratio of oxygen to ketone should not usually exceed 0.1:1. Preferably the molar ratio is below 0.01:1 and more preferably the process is carried out in the absence of oxygen.

The process of the invention can be carried out in the presence of water. The amount of water used is generally not critical, but it is preferably between 0.01 and 1 kg and more preferably between 0.05 and 0.2 kg of water per kg of cyclic ketone. The addition of water generally causes prolongation of the catalyst onstream time.

Suitable catalysts are theoretically all solids which undergo no change under the conditions of the reaction and have a surface area (BET) greater than 0.5 m²/g. Preferred catalysts have surface areas greater than 1 m²/g. There is theoretically no upper limit to the surface area that can be used, but for practical considerations the surface area (BET) will not usually exceed 2000 m²/g.

Accordingly, the surface area (BET) of the catalysts to be used in the present invention generally ranges from 0.5 to 2000, preferably from 1 to 500 and more preferably from 2 to 200 m²/g.

Particularly suitable catalyst compositions are oxidic materials. These primarily comprise catalysts containing or consisting of oxides of Group 2 to Group 14 elements.

Examples thereof are magnesium oxide, titanium(IV) oxide, zirconium(IV) oxide, chromium(III) oxide, cobalt oxide, copper oxide, zinc oxide, alumina and silicon dioxide.

The oxides can be uniform or mixed. Different oxides can form a homogeneous mixed oxide when precipitated together or they can exist in the form of a mechanically produced blend.

Other examples of catalytically active base materials having a large surface area are activated carbon and silicon nitride.

The aforementioned catalytic materials having a large surface area may contain, eg in amounts of from 0.01 to 5 wt %, compounds of Group 1, Group 15 and Group 16 elements. These elements are eg Na, K, P or S, usually in the form of their oxides.

Finally, metallic components, preferably likewise in the form of the oxides of Group 7 to Group 11 elements, may be aditionally applied, particularly in the case of said oxidic base materials. As examples thereof there may be mentioned rhenium, ruthenium, cobalt, rhodium, nickel, palladium, platinum, copper and silver.

Specifically, the following catalysts are suitable for example:

CuO, AgO, PdO, NiO, $Mn_2O_3$ or $Re_2O_7$
on ZnO, CaO, BaO, $SiO_2$ or $Al_2O_3$.

The preparation of these catalysts is carried out in known manner, for example by impregnation and calcination or by precipitation of hydroxides or carbonates followed by calcination, as described, for example, in Charles N.

Satterfield, Heterogeneous Catalysis in Industrial Practice, 2nd Edition, New York, McGraw Hill.

The process of the invention can be carried out over fixed or agitated catalysts. Examples of suitable reactor types are fixe-dbed reactors, fluidized-bed reactors and riser reactors.

When the catalyst activity falls, for example due to organic deposits, the catalyst, if of inorganic nature, can generally be fully regenerated by burning-off the sedimentation in air, eg at from 400° to 500° C.

The conversion can be carried out in a straight pass, the resulting mixture of products then being purified and any unconverted educt recycled, or the reaction product can be recycled to the reactor prior to purification in order to increase the conversion rate.

Cyclic enones such as cyclopentenone or cyclohexenone are sought-after intermediates for the preparation of pharmaceutical agents or agricultural pesticides.

The process of the invention is illustrated below with reference to the following examples, to which it is not restricted however. The percentages in the examples were determined by gas-chromato-graphic analysis.

EXAMPLE 1

Into a quartz tube equipped with external electric heating means there were filled ca 100 mL of ZnO (surface area (BET) 15 m$^2$/g; 3×5 mm extrudates), and ca 100 mL of glass rings were placed on top of the catalyst extrudates to form an evaporating zone. The reactor was brought to the desired reaction temperature by electric heating and the gas rate was set to 20 L(STP) of nitrogen per hour. Ca 20 mL/h of cyclopentanone were then introduced in trickling mode. The gaseous effluent was condensed by means of water cooling, and the collected product was then analyzed gaschromatographically. Table 1 gives the reaction temperatures and the resulting effluent compositions (wt %).

EXAMPLES 2–7

Example 1 was repeated using other catalysts, as listed in Table 1, to give the results stated. In Example 5, 4 L/h(STP) of air were metered in in addition to 20 L/h(STP) of nitrogen. The Cu rings used in Example 5 were treated with oxygen at 500° C. prior to the reaction. In Example 7 there was used cyclopentanone, which contained 5% of water.

TABLE 1

| Ex. | Catalyst | Temperature | Cyclo-pentanone | Cyclo-pentenone |
|---|---|---|---|---|
| 1 | ZnO surface area (BET) 15 m$^2$/g | 400 450 500 | 42 77 67 | 7.1 16 29 |
| 2 | CuO (20%)/ZnO (80%) surface area (BET) 15 m$^2$/g | 350 400 450 500 | 66 61 66 57 | 6.2 25.3 26.9 32.5 |
| 3 | CuO (17.5%)/SiO$_2$ surface area (BET) 29 m$^2$/g | 350 400 450 500 | 70 68 66 63 | 4.8 10.4 21 26 |
| 4 | CaO (44%)/ZnO (56%) surface area (BET) 15 m$^2$/g | 400 450 500 | 76 68 56 | 11 28 39 |
| 5 | Cu rings surface area (BET) 1 m$^2$/g | 450 500 | 96.7 92.2 | 2.7 6.6 |
| 6 | CuO (10%)/activated charcoal surface area (BET) 1000 m$^2$/g | 400 450 500 | 90.4 83.4 72.8 | 3.5 7.6 18.9 |

TABLE 1-continued

| Ex. | Catalyst | Temperature | Cyclo-pentanone | Cyclo-pentenone |
|---|---|---|---|---|
| 7 | ZnO surface area (BET) 15 m$^2$/g | 450 | 89 | 10.5 |
| 8 | Pd (9.5%)/Pt (0.5%)/ZrO$_2$ surface area (BET) 70 m$^2$/g | 400 | 79 | 8.5 |
| 9 | Fe$_2$O$_3$ (77%)/K$_2$O (12.5%)/WO$_3$ (3, 8%)/Ce$_2$O$_3$ (4, 7%)/CaO (2%) surface area (BET) 3.5 m$^2$/g | 400 | 93.7 | 3.1 |

EXAMPLE 10

In a manner as described in Example 1, cyclopentanone was converted at 500° C. over 100 mL of ZnO. Following ca 48 h of on-stream time at a feed rate of ca 1 liter per hour, the effluent was found to contain 85.1 wt % of cyclopentanone and 14.5 wt % of cyclopentenone. The collected effluents were subjected to distillation at 1013 mbar in a 40 cm packed column. There was obtained cyclopentenone having a purity of ca 99.6%.

EXAMPLE 11

As described in Example 1, cyclopentanone was caused to react at 400° C. over ZnO. Following a start-up phase of 0.5 h the reaction product was collected over a period of ca 20 h. It had the following composition: cyclopentanone 95.1 wt %, cyclopentenone 4.2 wt %. This mixture of products was then reused. The effluent was found to contain 92.5 wt % of cyclopentanone and 6.6 wt % of cyclopentenone.

EXAMPLE 12

Cycloheptanone was caused to react at 400° C. under the conditions of Example 2 (CuO/ZnO; surface area (BET) 15 m$^2$/g). The effluent was found to contain 95 wt % of unconverted educt, 1 wt % of cycloheptenone and 1.3 wt % of cresol and insignificant amounts of other products.

We claim:

1. A process for the preparation of cyclic, α,β-unsaturated ketones of formula II by dehydrogenation of cyclic ketones which form to formula I

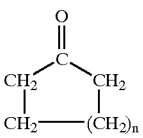

(I)

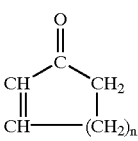

(II)

in which n denotes an integer from 1 to 10, and which may be substituted, at elevated temperature in the presence of a catalyst in the vapor phase, wherein the reaction is carried out in the absence of oxygen or in the presence of less than 0.1 mol of oxygen per mol of compound I at a temperature ranging from 250° to 600° C. and using a catalyst having a surface area (BET) of more than 0.5 m²/g.

2. A process as defined in claim 1, wherein the reaction is carried out under a pressure of from 0.1 to 10 bar.

3. A process as defined in claim 1, wherein the reaction is carried out in the presence of water.

4. A process as defined in claim 1, wherein the reaction is carried out in the presence of an oxidic catalyst.

5. A process as defined in claim 1, wherein the reaction is carried out in the presence of a catalyst containing or consisting of Group 2 to Group 14 oxides.

6. A process as defined in claim 5, wherein the reaction is carried out in the presence of a catalyst to which there has been additionally applied a Group 7 to Group 12 element or an oxide thereof.

7. A process as defined in claim 1, wherein the cyclic starting ketone of formula I used is cyclopentanone.

8. A process as defined in claim 1, wherein the cyclic starting ketone of formula I used is cyclohexanone.

* * * * *